United States Patent
Kobayashi et al.

(10) Patent No.: US 6,372,067 B1
(45) Date of Patent: Apr. 16, 2002

(54) PROCESS FOR MAKING ELASTICALLY STRETCHABLE COMPOSITE SHEET

(75) Inventors: Toshio Kobayashi; Hideyuki Ishikawa, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 91 days.

(21) Appl. No.: 09/610,590

(22) Filed: Jul. 5, 2000

(30) Foreign Application Priority Data

Jul. 5, 1999 (JP) ............................................. 11-190935

(51) Int. Cl.[7] .............................................. B32B 31/00
(52) U.S. Cl. ...................... 156/73.1; 156/229; 156/290; 156/308.4; 156/324
(58) Field of Search ................................ 156/73.1, 229, 156/290, 308.2, 308.4, 324, 494, 553, 580.1, 580.2, 583.1

(56) References Cited

U.S. PATENT DOCUMENTS 4,652,487 A * 3/1987 Morman ...................... 428/138
4,657,802 A * 4/1987 Morman ...................... 428/152
5,681,645 A * 10/1997 Strack et al. ............... 428/196

FOREIGN PATENT DOCUMENTS

| JP | 7-37703 | 4/1995 |
| WO | 92/16371 | 10/1992 |
| WO | 96/38620 | 12/1996 |

* cited by examiner

Primary Examiner—James Sells
(74) Attorney, Agent, or Firm—Lowe Hauptman Gilman & Berner, LLP

(57) ABSTRACT

A process for making an elastically stretchable composite sheet having a relatively low basis weight. An elastically stretchable second web is placed upon a first web comprising stretchable first continuous fibers and these first and second webs are intermittently bonded together at first bond regions to obtained a first composite web which is, in turn, stretched under a plastic deformation of the first continuous fibers and then elastically contracted. Thereafter, the first and second webs are supplementarily bonded together at second bond regions to obtain a second composite web as the elastically stretchable composite sheet.

11 Claims, 3 Drawing Sheets

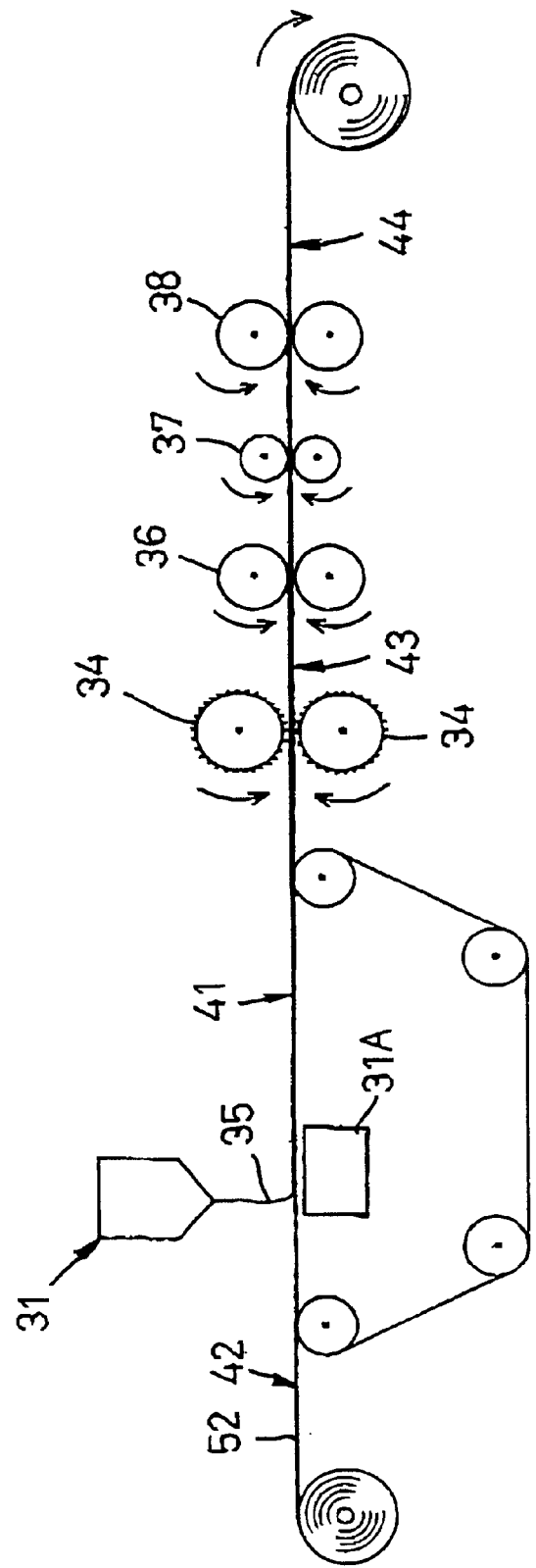

US 6,372,067 B1

PROCESS FOR MAKING ELASTICALLY STRETCHABLE COMPOSITE SHEET

BACKGROUND OF THE INVENTION

This invention relates to a process for making an elastically stretchable composite sheet and more particularly such a composite sheet offering a comfortable touch being suitable as an important component of disposable garments such as disposable diapers, sanitary napkins and disposable gowns used in medical site.

Japanese Patent Publication No. 1995-37703 discloses a process for making a nonwoven elastic sheet comprising the steps of continuously feeding elastic web with a tension in a machine direction, placing a fibrous web on the upper surface of the elastic web, bonding them together by heat- or ultrasonic-sealing and relaxing the elastic web to contract so that the fibrous web may form gathers. The nonwoven elastic sheet thus obtained has an elasticity generated by the presence of the elastic web and a comfortably soft touch so that such nonwoven elastic sheet may be suitably used as cover material of disposable diapers or sanitary napkins.

According to the process of prior art, the elastic web is relieved to contract first after the fibrous web has been bonded with the elastic web still under tension. With a consequence, the process of prior art is necessarily accompanied with a problem that a basis weight of the fibrous web being fed inevitably increases as the elastic web contracts after the fibrous web has been bonded with the elastic web.

SUMMARY OF THE INVENTION

This invention aims to provide a process for making an elastically stretchable composite sheet enabling the fibrous web in the finished composite sheet to maintain substantially the same basis weight as that of the fibrous web being fed and thereby to solve the problem in the process of prior art.

According to this invention, there is provided a process for making a composite sheet comprising a step of bonding a first web made of thermoplastic synthetic fibers and having an inelastic stretchability in one direction to at least one surface of a second web made of thermoplastic synthetic fibers having an elastic stretchability at least in the one direction and thereby to obtain the composite sheet having an elastic stretchability in said one direction, wherein:

the first web is made of stretchable synthetic continuous fibers having a breaking extension at least of 70% while the second web has its breaking extension higher than that of the first web and these first and second webs are bonded in accordance with the steps of:

a. continuously feeding the first web in the one direction;
 b. continuously feeding the second web in the one direction so as to be placed upon the first web;
 c. bonding the first and second webs placed upon each other together at first bond regions arranged intermittently at least along the one direction rather than in a direction which is orthogonal to the one direction;
 d. stretching the first and second webs bonded together at least in the one direction rather than the direction which is orthogonal to the one direction within a critical elasticity of the second web and a critical breaking extension of the first web; and
 e. elastically relaxing the stretched first and second webs to contract and then supplementarily bonding the first and second webs together at second bond regions arranged intermittently at least the one direction rather than the direction being orthogonal to the one direction and having a total area larger than a total area of the first bond regions to obtain the composite sheet.

BRIEF DESCRIPTION OF THE DRAWINGS

FIG. 3 is a diagram similar to FIG. 2 but illustrating steps of the process according to another embodiment of this invention for making the composite sheet.

DETAILED DESCRIPTION OF THE PREFERRED EMBODIMENTS

Details of a process for making the elastically stretchable composite sheet according to this invention will be more fully understood from the description given hereunder with reference to the accompanying drawings.

Figure 1:
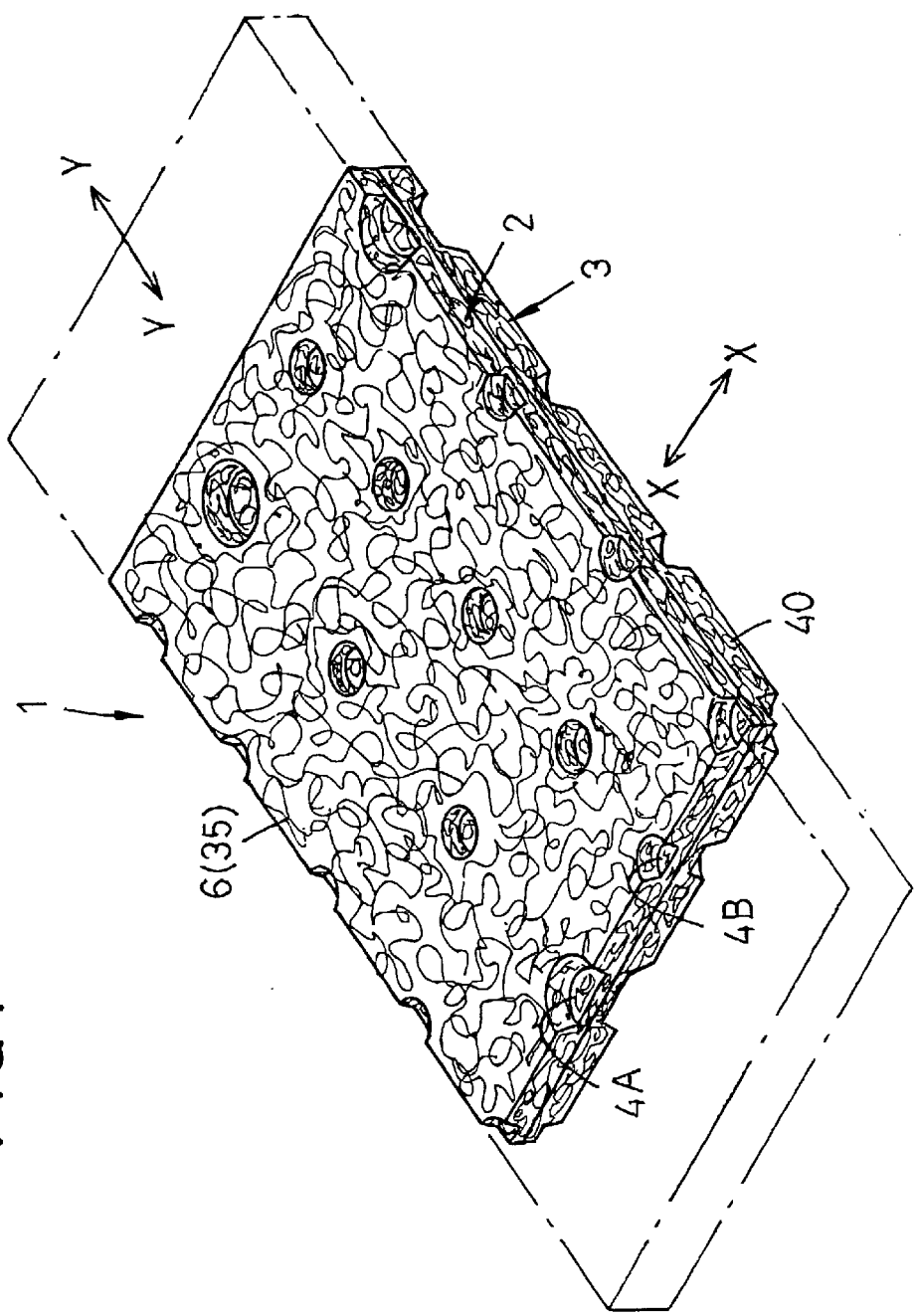
FIG. 1 is a perspective view showing an elastically stretchable composite sheet.

An elastically stretchable composite sheet 1 shown by FIG. 1 in a perspective view comprises an upper layer 2 and a lower layer 3 bonded together at first and second bond regions 4A, 4B. The composite sheet 1 is elastically stretchable and contractable at least in a direction indicated by a double-headed arrow Y—Y rather than in a direction indicated by a double-headed arrow X—X which is orthogonal to the direction Y—Y.

The upper layer 2 of the composite sheet 1 is inelastically stretchable at least in the direction Y—Y rather than in The direction X—X. This upper layer 2 is an assembly of thermoplastic synthetic resin continuous fibers 6. Preferably, the fibers 6 are bonded together only at the first and second bond regions 4 but not in the remaining region defined around the bond regions 4. In the remaining region extending around the first and second bond regions 4A, 4B, the continuous fibers 6 may extend over the upper surface of the lower layer 3 so as to describe irregular curves. In response to stretching of the composite sheet 1 in the direction Y—Y and/or in the direction X—X, the continuous fibers 6 describing the curves are reoriented to extend in the direction Y—Y and the upper layer 2 is inelastically stretched. The continuous fibers 6 may be of synthetic resin such as polypropyrene, polyester or polyethylene.

The lower layer 3 of the composite sheet 1 comprises a sheet which is elastically stretchable in the direction Y—Y, preferably both in the direction Y—Y and in the direction X—X. This sheet has a stretch ratio of at least 200%, preferably at least 400% in the direction Y—Y and elastically contractable by less than 1.3 times of its initial length after stretched by 100%. Such sheet may be a card web made of elastic threads, a nonwoven fabric such as a thermal bond nonwoven fabric or a spun lace nonwoven fabric, a woven fabric all made of elastic threads, or a film made of thermoplastic elastomer.

While both the first and second bond regions 4A, 4B may be individually dimensioned to have an area of 0.1~2 mm$^2$, FIG. 1 exemplarily shows a case in which the first bond region 4A has its area larger than the area of the second bond region 4B. In the composite sheet 1, the second bond regions 4B are preferably formed so that a total area of the second bond regions 4B may be larger than a total area of the first bond regions 4A.

The upper and lower layers 2, 3 may be bonded together at the first and second bond regions 4A, 4B by heating them together under a pressure or by ultrasonic-sealing them with each other. If a technique of mechanical entanglement is also useful to bond the continuous fibers 6 of the upper layer 2 with the component fibers of the lower layer 3, such mechanical entangling effect may be achieved by means of needle punching, high pressure columnar water streams or the like.

A initial force required to stretch such composite sheet 1, for example, in the direction Y—Y substantially corresponds to a force required to stretch the lower layer 3. The upper layer 2 has little influence upon the force required to stretch the composite sheet 1 since no significant force is required for the upper layer 2 to reorient its continuous fibers 6. Further stretching the composite sheet 1 with the lower layer being elastically deformed causes the continuous fibers 6 of the upper layer 2 still describing the curves to be further reoriented to be straightened in the region extending around the bond regions 4 in which the continuous fibers 6 are bonded to the lower layer 3. To stretch the composite sheet 1 further from such condition, a force is required, in addition to the force required to stretch the lower layer 3, to stretch said straightened continuous fibers 6.

Figure 2:
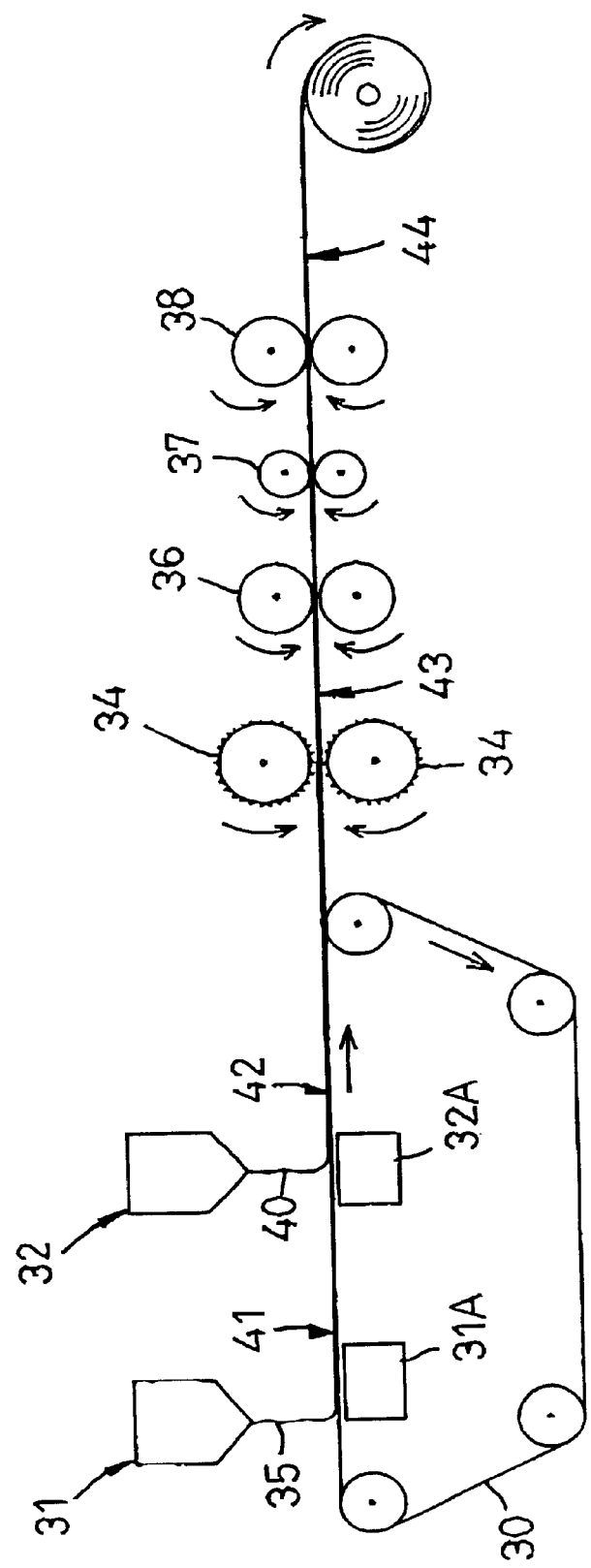
FIG. 2 is a diagram schematically illustrating the steps of a process according to an embodiment of this invention for making the composite sheet.

FIG. 2 is a diagram schematically illustrating a specific embodiment of the process for making the composite sheet 1. An endless belt 30 travels from the left hand toward the right hand as viewed in the diagram on the left hand, there is provided a first melt blown fiber molder 31 above the belt 30 below which there is provided a suction mechanism 31A. The first molder 31 includes a plurality of nozzles arranged transversely of the belt 30 and adapted to discharge first melt blown continuous fibers 35 of non-stretchable thermoplastic synthetic resin substantially in unstretched state. The continuous fibers 35 are accumulated on the belt 30 along irregular curves to form a first web 41. A discharge condition of the first molder 31 and a travelling condition of the belt 30 are selected so that the continuous fibers 35 stacked one upon another in the first web 41 may be prevented from being bonded together or, even if bonded together, the bonded continuous fibers 35 may be easily separated one from another on the subsequent step. Such unstretched first continuous fibers 35 have a breaking extension of at least 70%.

On the right side of the first molder 31, there are provided a second melt blown fiber molder 32 and a suction mechanism 32A. The second molder 32 also includes a plurality of nozzles arranged transversely of the belt 30 and adapted to discharge second melt blown continuous fibers 40 of elastically stretchable thermoplastic synthetic resin. The second melt blown continuous fibers 40 are accumulated on the first web 31 along irregular curves to form a second web 42. A discharge condition of the second molder 32 is selected so that the second continuous fibers 40 stacked one upon another may be bonded together and thereby form a sheet having an elastic stretchability in the travelling direction of the belt 30, preferably in the travelling direction as well as in the direction being orthogonal thereto. such second continuous fibers 40 have a breaking extension higher than that of the first continuous fibers 35.

The first and second webs 41, 42 placed upon each other are fed together to vertically paired embossing rolls 34, 34. The webs 41, 42 are thereby heated under a pressure at the first bond regions 4A arranged intermittently at least in the longitudinal direction corresponding to the direction in which the webs 41, 42 are fed rather than in the direction orthogonal to the longitudinal direction. In this manner, the webs 41, 42 are bonded together to form a first composite web 43. The first bond regions 4A are individually dimensioned, for example, in a range of 0.1–2 mm$^2$ and spaced one from another by 3~30 mm in the longitudinal direction as well as in the transverse direction. The first composite web 43 travels through first and second pairs of stretching rolls 36, 36; 37, 37. A revolution speed of the first pair of rolls 36, 36 is lower than a revolution speed of the second pair of rolls 37, 37. A difference of the revolution speeds between the first and second pairs of rolls 36, 36; 37, 37 is adjusted so that the first composite web 43 may be stretched by a predetermined stretch ratio, preferably by 50~300%, which is less than a breaking extension of the first web and within a critical elasticity of the second web 42. In the first composite web 43 stretched in this manner, the second web 42 is elastically stretched in the region extending around the first bond regions 4A while the first continuous fibers 35 are reoriented to the web travelling direction in the region extending around the first bond regions 4A and stretched under their plastic deformation. On such step of stretching, except the bond regions in which the two webs are bonded together by the pair of embossing rolls 34, 34, it is desirable that any sealing or mechanical entangling possibly occurring among the first continuous fibers 35 forming the first web 41 may be substantially loosened or disentangled. It is also desirable that bonding effect possibly occurring between the first continuous fibers 35 and the second web 42 may be practically eliminated.

A revolution speed of a third pair of rolls 38, 38 is the same as that of the first pair of rolls 36, 36 and the first composite web 43 is elastically contracted on the course defined between the second pair of rolls 37, 37 and the third pair of rolls 38, 38 to its initial length. The third pair of rolls 38, 38 serves also as the pair of embossing rolls by which the first composite web 43 contracted to its initial length is partially embossed to form a second composite web 44 having the second bond regions 4B. While each of the second bond regions 4B is shown to have substantially the same area as each of the first bond regions 4A has, a total area of the second bond regions 4B per unit area of the second composite web 44 is preferably larger than a total area of the first bond regions 4A per unit area of the second composite web 44 and more preferably corresponds to at least 1.3 times of the latter. The first bond regions 4A are individually dimensioned, for example, in a range of 0.1–2 mm$^2$ and spaced one from another by 0.5~5 mm in the longitudinal direction as well as in the transverse direction. It should be understood that this invention may exploit even with some of the second bond regions 4B placed upon some of the first bond regions 4A. The second composite web 44 is taken up in the form of a roll and subsequently is cut into a desired dimension to obtain the individual composite sheets 1. The first continuous fibers 35 in the second composite web 44 correspond to the continuous fibers 6 of FIG. 1 and the first web 41 comprising these fibers 6 corresponds to the upper layer 2 of FIG. 1. The second web 42 in the second composite web 44 corresponds to the lower layer 3 of FIG. 1. This invention may also exploit by using the third pair of rolls 38, 38 merely as a pair of feeding rolls just like the first pair of rolls 36, 36 and by providing a second pair of embossing rolls behind the third pair of rolls 38, 38.

On the starting step, the first continuous fibers 35 are discharged in their substantially or completely unstretched state onto the belt 30 and, on the subsequent step, the first continuous fibers 35 are stretched under a plastic deformation at a room temperature of 10–60° C., more preferably of 15–40° C. While such first melt blown fibers 35 are preferably used in this invention, this invention can be effectively exploit even using stretched threads in the place of the unstretched thread so far as the stretched threads are stretchable at the room temperature.

When the second composite web 44 obtained in this manner is stretched after the first and second webs 41, 42 have previously been bonded together at the first bond regions 4A, the component fibers of the first web 41 bonded together or entangled together are loosened. Thereby uneven distribution of the first continuous fibers 35 in the first web 41 due to such bonding or entanglement is eliminated and, with a consequence, the second composite web 44 offering an even touch is obtained.

In the course of the process for making the composite sheet, it is also possible to stretch the first composite web 43 in the transverse direction orthogonal to the direction in which the first composite web 43 travels. In this case, only the portion of the first continuous fibers 35 extending transversely of the first web 41 can be stretched since the first and second webs 41, 42 have previously been bonded together. In the second composite web 44, the second bond regions 4B function to bond the first web of which the unevenness of fiber distribution has been eliminated to the second web 42 so firmly that the two webs 41, 42 might be separated from each other even when the second composite web 44 is repetitively stretched.

Even when the second web 42 includes rubber-based material, the first web 41 may used so as to come in contact with the wearer's skin to prevent a poor slidability peculiar to rubber material from stimulating the wearer's skin. With the arrangement of the second composite web 44 in which, except the first and second bond regions 4A, 4B, the first continuous fibers 35 of the second composite web 44 are bonded neither with themselves nor with the second web 42, a relatively small force required to stretch the second web 42 alone is sufficient as an initial force required to stretch the second composite web 44. Accordingly, the easily stretchable soft sheet is formed by the second composite web 44 in spite of its two-layered construction. The process according to the embodiment of FIG. 2 allows the first and second webs 41, 42 of the second composite web 44 to maintain their respective basis weights immediately after they have been discharged from the respective molders 31, 32. Additionally, the second composite web 44 generally presents a high breathability since both the first and second webs 41, 42 comprise fibrous assemblies.

The steps of the process illustrated by FIG. 2 may be modified in various manners to exploit this invention. For example, it is possible to feed the second web 42 onto the belt 30 before the first web 41 is fed onto the belt 30. It is also possible to use, in addition to the pair of embossing rolls 34, 34, the other means such as needle punching or high pressure columnar water streams in order to bond the first and second webs 41, 42. Alternatively, a third molder is provided downstream of the second molder 32 so that non-stretchable third melt blown continuous fibers discharged from this third molder may form a third web similar to the first web 41 on the second web 42 and thereby form a three-layered composite sheet 1 comprising, in addition to the first and second webs 41, 42, a third web. The first web 41 and this third web may be either identical to each other or different from each other in type of resin, fineness, and appearance inclusive of color.

FIG. 3 is a diagram similar to FIG. 2 but illustrating another preferred embodiment of the process according to this invention. According to this embodiment, a film 52 made of thermoplastic elastomer and having an elastic stretchability in the travelling direction of the belt 30 is fed as the second web 42 from the left hand of FIG. 3 and the first web 41 comprising the first continuous fibers 35 is fed onto said film 52. The first and second webs 41, 42 travel to the pair of embossing rolls 34, 34 in the same manner as in FIG. 2, between which the webs 41, 42 are intermittently bonded together at the second bond regions 4B to form a second composite web 44. On the step of bonding the first web 41 with the second web 42 in the form of the film 52 to form the first and second bond regions 4A, 4B, the area of the individual bond regions 4A, 4B can be dimensioned as small as in the order of 0.03–1 mm$^2$ without an apprehension that the first and second webs 41, 42 might be easily separated from each other. It should be understood here that the area of the individual bond regions 4A, 4B can be selectively varied in a range of 0.03–10 mm$^2$ without departing from the scope of this invention.

The composite sheet 1 obtained by the process according to this invention is easily stretchable and offers a comfortable touch, so that the composite sheet 1 is suitable as cloth and/or elastic member in disposable garments such as disposable pants or disposable gowns used in medical site.

The process according to this invention for making the elastically stretchable composite sheet enables the fibrous web in the composite sheet to have a basis weight lower than that in the conventional composite sheet because the stretchable fibrous web is laminated in its unstretched condition with the elastically stretchable web. Furthermore, the process according to this invention enables the fibrous web to be evenly stretched since the process by bonding the stretchable web to the elastically stretchable web on two steps, i.e., before and after the step of stretching the composite sheet.

In the course of stretching the composite sheet, the component fibers of the fibrous web are stretched under a plastic deformation and, at the same time, undesirable bonding and/or entangling among the component fibers themselves in the fibrous web and undesirable sealing between the fibrous web and the elastically stretchable web are loosened. Therefore, a relatively small force required to stretch the elastically stretchable web alone is sufficient as an initial force required to stretch the composite sheet so that the composite sheet may be easily stretched and offer a comfortable soft touch.

What is claimed is:

1. A process for making a composite sheet generally comprising a step of bonding a first web made of thermoplastic synthetic fibers and having an inelastic stretchability in one direction to at least one surface of a second web made of thermoplastic synthetic fibers having an elastic stretchability at least in said one direction and thereby to obtain the composite sheet having an elastic stretchability in said one direction, wherein:

said first web is made of stretchable synthetic continuous fibers having a breaking extension at least of 70% while said second web has its breaking extension higher than that of said first web and said first and second webs are bonded in accordance with the steps of:

a) continuously feeding said first web in said one direction;

b) continuously feeding said second web in said one direction so as to be placed upon said first web;

c) bonding said first and second webs placed upon each other together at first bond regions arranged intermittently at least along said one direction rather than in a direction which is orthogonal to said one direction;

d) stretching said first and second webs bonded together at least in said one direction rather than the direction which is orthogonal to said one direction within a critical elasticity of said second web and a critical breaking extension of said first web; and e) elastically relaxing said stretched first and second webs to contract and then supplementarily bonding said first and second webs together at second bond regions arranged intermittently at least said one direction rather than said direction being orthogonal to said one direction and having a total area larger than a total area of said first bond regions to obtain said composite sheet.

2. The process according to claim 1, wherein said second web is any one of an elastically stretchable nonwoven fabric, a woven fabric and a stretchable film.

3. The process according to claim 1, wherein said second web is made of elastically stretchable threads.

4. The process according to claim 1, wherein said second web is made of melt blown fibers.

5. The process according to claim 1, wherein said first web is made of melt blown fibers.

6. The process according to claim 1, wherein said step d includes a step of elastically stretching said second web and simultaneously stretching the synthetic fibers of said first web to induce its plastic deformation occurring longitudinally of said first web.

7. The process according to claim 1, wherein said step d further includes a step of loosening the synthetic fibers of said first web having been bonded together on said step of c except those having been bonded to the second web on said step c.

8. The process according to claim 1, wherein said first and second webs are bonded together using any one of heat-sealing, ultrasonic-sealing, needle punching and high pressure columnar water streams.

9. The process according to claim 1, wherein a pair of said first webs are bonded to both surfaces of said second web, respectively.

10. The process according to claim 9, wherein said respective first webs bonded to both surfaces of said second web are different from each other in any one of basis weight, type of fibers and appearance.

11. The process according to claim 1, wherein, in said one direction as well as in said direction being orthogonal to said one direction, each pair of adjacent said first bond regions are spaced from each other by 3–30 mm while each pair of adjacent said second bond regions are spaced from each other by 0.5–5 mm.

* * * * *